United States Patent [19]

Baldwin et al.

[11] Patent Number: 5,756,810
[45] Date of Patent: May 26, 1998

[54] PROCESS OF PREPARING 3-NITRO BENZOATE COMPOUNDS IN LOWER ALKANOL

[75] Inventors: John J. Baldwin, Gwynedd Valley, Pa.; Michael H. J. Ohlmeyer; Ian Henderson, both of Plainsboro, N.J.

[73] Assignee: Pharmacopeia, Inc., Princeton, N.J.

[21] Appl. No.: 714,065

[22] PCT Filed: Mar. 10, 1995

[86] PCT No.: PCT/US95/03223

§ 371 Date: Sep. 11, 1996

§ 102(e) Date: Sep. 11, 1996

[87] PCT Pub. No.: WO95/24186

PCT Pub. Date: Sep. 14, 1995

[51] Int. Cl.⁶ .................................................. C07C 205/01
[52] U.S. Cl. .................................................. 560/20; 560/23
[58] Field of Search .................................................. 560/20, 23

[56] References Cited

U.S. PATENT DOCUMENTS 5,281,585   1/1994   Duggan et al. .......................... 514/317

FOREIGN PATENT DOCUMENTS

| | | |
|---|---|---|
| 0 127 124 A | 12/1984 | European Pat. Off. . |
| 0 276 101 A | 7/1988 | European Pat. Off. . |
| 0 529 568 A | 3/1993 | European Pat. Off. . |
| 0 585 155 A | 3/1994 | European Pat. Off. . |
| 92/00091 A | 1/1992 | WIPO . |
| WO 93/06121 | 4/1993 | WIPO . |
| WO 93/20242 | 10/1993 | WIPO . |
| WO 94/08051 | 4/1994 | WIPO . |

OTHER PUBLICATIONS

Barany et al, JACS, vol. 107, No. 17, 1985, pp. 4936–4942.

Angelastro et al., Inhibition of Human Neutrophil Elastase with Peptidyl Electrophilic Ketones. 2. Orally Active $P_G$–Val–Pro–Val Pentafluoroethyl Ketones, J. Med. Chem., 37(26) 4538–53, 1994.

Gubert, S. et al., Synthesis and Pharmacological Screening of New Angiotensin Converting Enzyme Inhibitors, Farmaco, 45(1), 59–79, 1990.

Ponticello et al., J. Med. Chem., 3.0, 591–597, 1987.

Brenner and Lerner, Proc. Natl. Acad. Sci., 8 9, 5381–5383, Jun. 1992.

Ohlmeyer et al., Proc. Nat'l. Acad. Sci. 9 0, 10922–10926, Dec. 1993.

Chen et al., J. Chem. Soc., 116, 2261–2262, 1994.

*Primary Examiner*—Zinna Northington Davis
*Attorney, Agent, or Firm*—Heslin & Rothenberg, PC

[57] ABSTRACT

A process for preparing t-butyl 4-(hydroxymethyl)-3-nitrobenzoate from t-butyl 4-(acetoxymethyl)-3-nitrobenzoate which comprises reacting t-butyl 4-(acetoxymethyl)-3-nitrobenzoate with hydrazine or hydrazine hydrate in a lower alkanol at 0°–50° C.

4 Claims, No Drawings

PROCESS OF PREPARING 3-NITRO BENZOATE COMPOUNDS IN LOWER ALKANOL

This application is a 371 PCT/US95/03223 filed Mar. 10, 1995

BACKGROUND OF THE INVENTION

There is interest in methods for the synthesis of large numbers of diverse compounds which can be screened for various possible physiological or other activities. Techniques have been developed in which one adds individual units sequentially as part of the chemical synthesis to produce all or a substantial number of the possible compounds which can result from all the different choices possible at each sequential stage of the synthesis. For these techniques to be successful, it is necessary for the compounds to be amenable to methods by which one can determine the structure of the compounds so made. Brenner and Lerner (PNAS USA 81: 5381–83 (1992)) and WO 93/20242, for example, describe a synthesis wherein oligonucleotides are produced in parallel with and are chemically linked as genetic tags to oligopeptides as the compounds of interest. WO 93/06121 teaches methods for particles-based synthesis of random oligomers wherein identification tags on the particles are used to facilitate identification of the oligomer sequence synthesized. A detachable tagging system is described in Ohlmeyer et al., *Proc. Natl. Acad. Sci. USA*, 90p10922–10926, December 1993.

SUMMARY OF THE INVENTION

The present invention relates to combinatorial chemical libraries of compounds encoded with tags and to the use of these libraries in assays to discover biologically active compounds. The present invention also relates to libraries containing aryl sulfonamides, N-acyl derivatives, and N-substituted pyrrolidines and piperidines and using these libraries to identify biologically active members by screening for inhibition of serine proteases such as thrombin and Factor $X_a$; metallo proteases such as angiotensin converting enzyme (ACE); and carbonic anhydrase isozymes. The present invention also relates to members of the library which are inhibitors of carbonic anhydrase and thrombin. The invention also relates to methods for their preparation, intermediates, and to methods and pharmaceutical formulations for using these aryl sulfonamides, N-acyl derivatives, and N-substituted pyrrolidines and piperidines in the treatment of mammals, especially humans.

Because of their activity as inhibitors of serine proteases and carbonic anhydrase isozymes, the compounds of the present invention are useful in the treatment of hypercoagulation disease, post-myocardial infarction treatment, post-angioplasty treatment, and ocular diseases such as glaucoma.

DETAILED DESCRIPTION OF THE INVENTION

The combinatorial libraries of the present invention are represented by Formula I:

wherein:

Ⓢ is a solid support;

T'—L— is an identifier residue;

—L'—II' is a ligand/linker residue; and q is 3–30.

Preferred compounds of Formula I are those wherein: T'—L— is of the Formula:

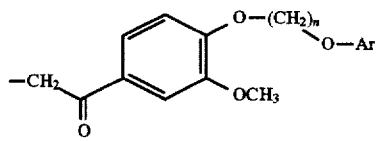

wherein n=3–12 when Ar is pentachlorophenyl and
n=4–6 when Ar is 2,4,6-trichlorophenyl;

q is 3–13; and

—L'— is

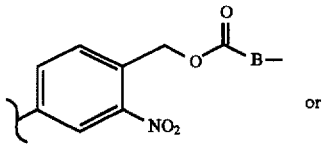

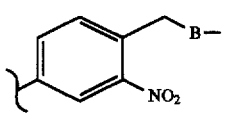

wherein the left-hand bond as shown is the point of attachment to the solid support and the right hand bond is the point of attachment to the ligand, and B is O or NH, with the proviso that in (b) B is NH when attached to a carbonyl group in the ligand.

Depending on the choice of L' (see Table 1), the ligands of Formula II may be detached by photolytic, oxidative, or other cleavage techniques. For example, when —L'— is (a) and B is O, photolytic detachment may be represented by:

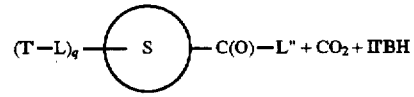

wherein L" is the residue from L' and II'BH is II.

Therefore, compounds of the present invention are also represented by Formula II $$Y—A—CO—R^1 \qquad\qquad II$$

wherein:

$R^1$ is —N($R^6$)—$(CH_2)_{2-5}$—Z—$(CH_2)_{2-5}$—$R^9$, —NH$(CH_2)_{2-5}$—$R^9$,

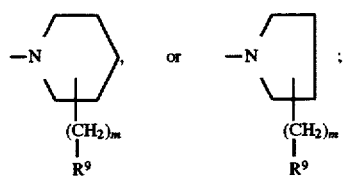

$R^2$ is the residue on the α carbon of methionine, O-t-butyl-serine, serine, S-trityl-cysteine, cysteine, aspartic acid-β-t-butyl ester, aspartic acid, glutamic acid-γ-t-butyl ester, glutamic acid, $N^{im}$-trityl-histidine, histidine, $N^ε$-Boc-lysine, lysine, $N^g$-Mtr-arginine, arginine, N-β-trityl-asparagine, asparagine, N-γ-trityl-glutamine, glutamine, $N^{in}$-Boc-tryptophan, tryptophan, isoleucine, phenylalanine, glycine, alanine, valine, or leucine;

$R^3$ is lower alkyl or —$(CH_2)_m$—Q—X;

$R^4$ is —Q($R^7$, $R^8$)—$SO_2NH_2$, —$(CH_2)_m$—$R^{10}$, with the proviso that when m=0, $R^{10}$ is not OH, lower alkyl, a 6-membered aromatic heterocyclic ring containing 1 or 2 N atoms, heteroaryl-lower alkyl,

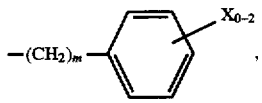

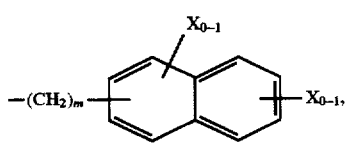

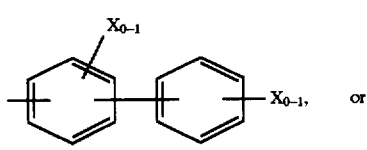

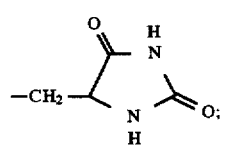

$R^5$ is lower alkyl, lower cycloalkyl, alkenyl, alkynyl, a mono- or bicyclic 6- to 10-membered aromatic ring system, or a mono- or bicyclic 5- to 10-membered heteroaromatic ring system containing 1 or 2N atoms, either system unsubstituted or substituted with 1–2 substituents selected from halogen, alkoxy, alkyl, $CF_3$, CN, —N(lower alkyl)$_2$, and acylamino;

$R^6$ is H or lower alkyl;

$R^7$, $R^8$ is each independently H, halogen, lower alkyl, alkoxy, CN, —$NO_2$, —CO-lower alkyl, —N(lower alkyl)$_2$, or NH—CO-lower alkyl;

$R^9$ is OH, $CONH_2$, or COOH;

$R^{10}$ is alkoxy, OH, or COOH;

m is 0–6;

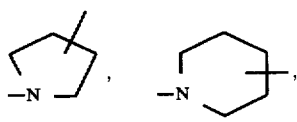

A is —NH—$CHR^2$—, —NH$(CH_2)_{2-12}$—, or the descarboxy residue of a primary or secondary amino acid;

Q is a 5- or 6-membered aromatic or heteroaromatic ring containing 0–3 heteroatoms selected from O, N, and S, or a bicyclic 9- or 10-membered aromatic or heteroaromatic ring system containing 0–3 heteroatoms selected from O, N, and S;

X is H, lower alkyl, halogen, alkoxy, $CF_3$, CN, —$NO_2$, —CO-lower alkyl, —N(lower alkyl)$_2$, NH—CO-lower alkyl, or COOH;

Y is —$SO_2R^3$, —$COR^4$, —CO—CH($R^2$)—$NHSO_2R^3$, —CO—CH($R^2$)—$NHCOR^4$, —CO—$NHR^5$, or —$COOR^5$; and Z is —O—, —S—, or —N(lower alkyl)—;

or a pharmaceutically acceptable salt thereof.

A preferred embodiment of the invention is a compound of Formula II wherein:

Y is

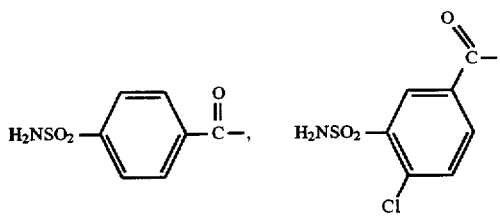

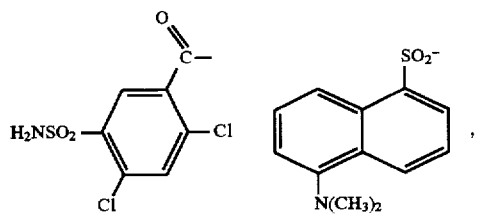

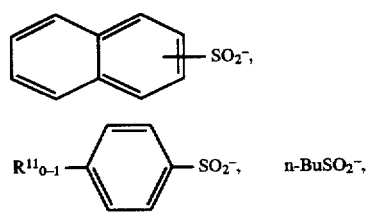

wherein $R^{11}$ is $CH_3$, $(CH_3)_3C$—, or Cl;

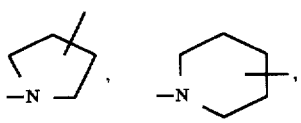

A is —NH—$CHR^2$—, —NH$(CH_2)_{2-12}$—, or the descarboxy residue of a primary or secondary amino acid; and $R^1$ is

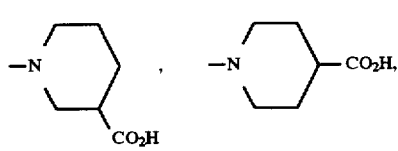

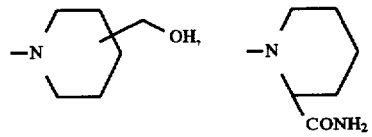

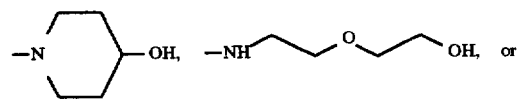

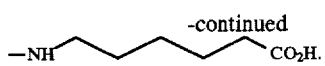

Another preferred embodiment of the invention is a compound of Formula II wherein:
Y is

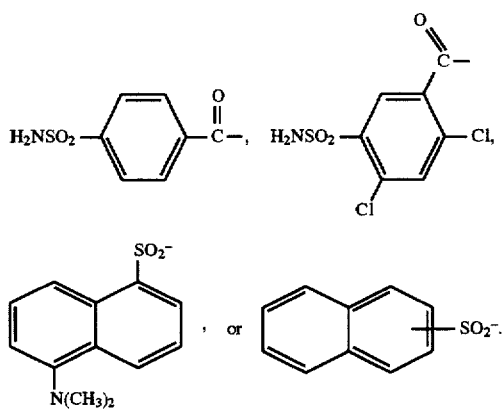

One embodiment of the invention is the use of the combinatorial library of Formula I in assays to discover biologically active compounds (ligands) of Formula II. Thus, an aspect of the invention is a method of identifying a compound having a desired characteristic which comprises synthesizing a combinatorial library of Formula I and testing the compounds of Formula I and the ligands of Formula II, either attached to the solid support or detached therefrom in an assay which identifies compounds having the desired characteristic. A further embodiment of the invention is determining the structure of any compound so identified.

Another embodiment of the invention is an improved process for preparing t-butyl 4-(hydroxymethyl)-3-nitrobenzoate from t-butyl 4-(acetoxymethyl)-3-nitrobenzoate which comprises hydrazinolysis of the acetoxymethyl-nitrobenzoate using hydrazine or hydrazine hydrates in polar solvents such as lower alkanols, e.g. methanol and isopropanol, and aprotic polar solvents such as acetonitrile at 0°–50° C. The improved process produces the hydroxymethyl-nitrobenzoate in nearly quantitative yield. When 4-(acetoxymethyl)-3-nitrobenzoic acid is linked to the solid support., the improved process for removing the alcohol protecting group, i.e., with hydrazine and methanol, is highly superior to the prior art methods.

Another embodiment of the invention is the use of divinylbenzene-cross-linked, polyethyleneglycol-grafted polystyrene beads optionally functionalized with amino groups (for example, TentaGel® S $NH_2$, Rapp Polymere) as the solid supports for constructing combinatorial libraries. Use of these beads greatly enhances the yield of ligands, e.g., compounds of Formula II, detached from the solid supports. Yields of ligands from supports such as DVB-crosslinked polystyrene are relatively low (<10%). The use of DVB-crosslinked, PEG-grafted polystyrene produces yields of >60%.

Definitions

The following abbreviations have the indicated meaning:
c-=cyclo
DEAD=diethylazodicarboxylate
DCM=dichloromethane=methylene chloride
DIC=diisopropylcarbodiimide
DMAP=4-N,N-dimethylaminopyridine
DMF=N,N-dimethylformamide
DVB=1,4-divinylbenzene
EDT=ethane dithiol
FACS=fluorescence activated cell sorting
Fmoc=9-fluorenylmethoxycarbonyl
GC=gas chromatography
HOBt=N-hydroxybenzotriazole
im=imidazole
in=indole
m-=meta
Me=methyl
Mtr=4-methoxy-2,3,6-trimethylbenzenesulfonyl
PEG=polyethylene glycol
Ph=phenyl
r.t.=room temperature
sat'd=saturated
s-=secondary
t-=tertiary
TFA=trifluoroacetic acid
THF=tetrahydrofuran Alkyl is intended to include linear, branched, or cyclic structures and combinations thereof. "Lower alkyl" includes alkyl groups of from 1 to 8 carbon atoms. Examples of lower alkyl groups include methyl, ethyl, propyl, isopropyl, butyl, s- and t-butyl, pentyl, hexyl, octyl, and the like. "Lower cycloalkyl" includes cycloalkyl groups of from 3 to 8 carbon atoms. Examples of lower cycloalkyl groups include c-propyl, c-butyl, c-pentyl, 2-methylcyclopropyl, cyclopropylmethyl, adamantly, and the like.

"Alkenyl" is $C_3$–$C_6$ alkenyl of a linear, branched, or cyclic ($C_5$–$C_6$) configuration and combinations thereof. Examples of alkenyl groups include allyl, isopropenyl, pentenyl, hexenyl, c-hexenyl, 1-propenyl, 2-butenyl, 2-methyl-2-butenyl, and the like.

"Alkynyl" is $C_3$–$C_6$ alkynyl of a linear or branched configuration and combinations thereof. Examples of alkenyl groups include propyne, butyne, pentyne, 3-methyl-1-butyne, 3,3-dimethyl-1-butyne, and the like.

"Alkoxy" means alkoxy groups of from 1 to 6 carbon atoms of a straight, branched, or cyclic configuration. Examples of alkoxy groups include methoxy, ethoxy, propoxy, isopropoxy, cyclopropyloxy, cyclohexyloxy, and the like.

"Acylamino" means acylamino groups of from 1 to 6 carbon atoms of a straight, branched or cyclic configuration. Examples of acylamino groups are acetylamino, butylamino, cyclohexylamino, and the like.

Halogen includes F, Cl, Br, and I.

$R^2$ is intended to include racemates and all optical isomers. The amino acid residues of $R^2$ are, for example, methyl (alanine), hydroxymethyl (serine), phenylmethyl (phenylalanine), thiomethyl (cysteine), carboxyethyl (glutamic acid), etc.

In $R^4$, "heteroaryl" means an aromatic 5- to 10-membered mono- or bicyclic heterocyclic ring system containing 1 or 2N atoms, the systems either unsubstituted or substituted with 1–2 substituents selected from halogen, alkoxy, alkyl, $CF_3$, CN, —N(lower alkyl)$_2$, and acylamino;

In $R^5$, the aromatic 6- to 10-membered carbocyclic rings include benzene and naphthalene and the 5- to 10-membered aromatic heterocyclic rings include imidazole, pyridine, and indole.

In A, the primary or secondary amino acids are intended to include alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine, valine, sarcosine, L-alanine, chloro-L-alanine hydrochloride, 2-aminoisobutyric acid, 2-(methylamino)isobutyric acid, DL-3-aminoisobutyric acid, DL-2-aminoisobutyric acid, (R)-(-)-2-aminoisobutyric acid, (S)-(+)-2-aminoisobutyric acid, D)-t-leucine, L-t-leucine, D-norvaline, L-norvaline, L-2-amino-4-pentenoic acid, D-isoleucine, L-isoleucine, D-norleucine, 2,3-diaminopropionic acid monohydrochloride, L-norleucine, DL-2-aminocarprylic acid, β-alanine, DL-3-aminobutyric acid, 4-aminobutyric acid, 4-(methylamino)butyric acid hydrochloride, 5-aminovaleric acid, 7-aminoheptanoic acid, 8-aminocaprylic acid, 11-aminodecanoic acid, 12-aminododecanoic acid, carboxymethoxylamine hemihydrate, D-serine, D-homoserine, L-homoserine, L-(+)-canavaninesulfate homohydrate, D-allothreonine, L-allothreonine, D-threonine, L-threonine, DL-4-amino-3-hydroxybutyric acid, DL-3-hydroxynorvaline, (3S,4S)-(-)-statine, 5-hydroxy-DL-lysine hydrochloride, 5-aminoleucinic acid hydrochloride, 1-amino-1-cyclopropanecarboxylic acid, 1-amino-1-cyclopentanecarboxylic acid, 1-amino-1-cyclohexanecarboxylic acid, 5-amino-1,3-cyclohexadiene-1-carboxylic acid hydrochloride, 2-amino-2-norbornanecarboxylic acid, (S)-(-)-2-azetidinecarboxylic acid, cis-4-hydroxy-D-proline, cis-4-hydroxy-L-proline, trans-4hydroxy-L-proline, 3,4-dehydro-DL-proline, 3,4-dehydro-L-proline, D-pipecolinic acid, L-pipecolinic acid, mimosine, 2,3-diaminopropionic acid monohydrobromide, DL-2,4-diaminobutyric acid dihydrochloride, (S)-(+)-diaminobutyric acid hydrochloride, D-ornithine hydrochloride, L-ornithine hydrochloride, 2-methylornithine hydrochloride monohydrate, N-ε-methyl-L-lysine hydrochloride, N-methyl-D-aspartic acid monohydrate, DL--2-methylglutamic acid hemihydrate, DL-2-aminoadipic acid, D-2-aminoadipic acid, L-2-aminoadipic acid, (±)-3-aminoadipic acid, D-cysteine hydrochloride monohydrate, D-penicillamine, L-penicillamine, DL-homocysteine, S-methyl-L-cysteine, L-methionine, D-ethionine, L-ethionine, S-carboxymethyl-L-cysteine, (S)-(+)-2-phenylglycine, (R)-(—)-2-phenylglycine, N-phenylglychie, N-(4 hydroxyphenyl) glycine, D-phenylalanine, (S)-(-)-indoline-2-carboxylic acid, α-methyl,DL-phenylalanine, β-methyl-DL-phenylalanine hydrochloride, D-homophenylalanine, L-homophenylalanine, DL-2-fluorophenylglycine, DL-2-fluorophenylalanine, DL-3-fluorophenylalanine, DL-4-fluorophenylalanine, DL-4-chlorophenylalanine, L-4-chlorophenylalanine, 4bromo-DL-phenylalanine, 4-iodo-D-phenylalanine, 3,3',5-triiodoL,-thyronine, (+)-3,3',5-triiodo-L-thyronine sodium salt, D-thyronine, L-thyronine, DL-m-tyrosine, D4-hydroxyphenylglycine, D-tyrosine, L-tyrosine, o-methyl-L-tyrosine, 3-fluoro-DL-tyrosine, 3-iodo-L-tyrosine, 3-nitro-L-tyrosine, 3,5-diiodo-L-tyrosine dihydrate, DL-dopa, L-dopa, 2,4,5-trihydroxyphenyl-DL-alanine, 3-amino-L-tyrosine dihydrochloride monohydrate, 4-amino-D-phenylalanine hydrate, 4-amino-L-phenylalanine hydrate, 4amino-DL-phenylalanine hydrate, 4-nitro-L-phenylalanine monohydrate, 4-nitro-DL-phenylalanine, 3,5-dinitro-L-tyrosine monohydrate, DL-α-methyltyrosine, L-α-methyltyrosine, (-)-3-(3,4-dihydroxyphenyl)-2-methyl-L-alanine sesquihydrate, DL-threo-3-phenylserine hydrate, and DL-DOPS.

Q is intended to include phenyl, thienyl, furanyl, thiadiazolyl, pyridyl, and pyrimidyl.

L and L' are depicted in Table 1, which also shows cleavage reagents. In designing a synthetic scheme, L and L' are chosen such that they are orthogonally reactive, i.e., they must allow for removal of either T or II (where T=T'—OH) without removal of the other since simultaneous cleavage of both T and II from the solid support is disadvantageous. In the structures as shown, the left-hand bond is the point of attachment to the solid support and the right-hand bond is the point of attachment to either T or II.

The tags of this invention, T, are chemical entities which possess several properties: they must be detachable from the solid supports, preferably by photolysis or oxidation; they must be individually differentiable, and preferably separable; they must be stable under the synthetic conditions; they must be capable of being detected at very low concentrations, e.g., $10^{-18}$ to $10^{-9}$ mole; they should be identifiable with readily-available equipment which does not require sophisticated technical capabilities to operate; and they should be relatively economical. The tags may be structurally related or unrelated, e.g., a homologous series, repetitive functional groups, related members of the Periodic Chart, different isotopes,, combinations thereof, and the like. At the end of the combinatorial synthesis, to each solid support, there will usually be attached at least 0.01 femtomol, usually 0.001–50 pmol, of each tag. The tags may be aliphatic, alicyclic, aromatic, heterocyclic, or combinations thereof. Distinguishing features may be the number of repetitive units, such as methylene groups in an alkyl moiety; alkyleneoxy groups in a polyalkyleneoxy moiety; halo groups in a polyhalo compound; α- and/or β-substituted ethylene groups where the substituents may be alkyl groups, oxy, carboxy, amino, halo, or the like; isotopes; etc.

The materials upon which the combinatorial syntheses of the invention are performed are referred to as solid supports, beads, and resins. These terms are intended to include:

a) beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and b) soluble supports such as low molecular weight non-cross-linked polystyrene.

It is intended that the definitions of any substituent or symbol (e.g., $R^2$, $R^8$, m, etc.) in a particular molecule be independent of its definitions elsewhere in the molecule.

TABLE 1

| LINKER GROUPS | |
|---|---|
| Linker Group | Cleavage Reagent |
| 1. NO₂ / —CH₂B— or | hv |

TABLE 1-continued

LINKER GROUPS

| Linker Group | Cleavage Reagent |
|---|---|
| 1. 4-NO$_2$-benzyl-O-C(=O)-B— (aryl with NO$_2$ and CH$_2$O-C(=O)-B—) | |
| 2. 2-O$_2$N-aryl-CH$_2$O— | hv |
| 3. aryl(OR)-O— | Ce(NH$_4$)$_2$(NO$_3$)$_6$ |
| 4. RO-aryl-O— | Ce(NH$_4$)$_2$(NO$_3$)$_6$ |
| 5. —CH=CH(CH$_2$)$_2$— | O$_3$, OsO$_4$/IO$_4^-$, or KMnO$_4$ |
| 6. —CH=CHCH$_2$— | O$_3$, OsO$_4$/IO$_4^-$, or KMnO$_4$ |
| 7. —CH$_2$CH=CH— | O$_3$, OsO$_4$/IO$_4^-$, or KMnO$_4$ |
| 8. furan (O in ring)-O— | 1) O$_2$ or Br$_2$, MeOH  2) H$_3$O$^+$ |
| 9. —CH=CHCH$_2$O— | (Ph$_3$P)$_3$RhCl(H) |
| 10. aryl(Br)-O— | Li, Mg, or BuLi |
| 11. —S—CH$_2$—O— | Hg$^{+2}$ |
| 12. X-CH$_2$—O— | Zn or Mg |
| 13. OH-CH$_2$—O— | Oxidation, e.g., Pb(OAc)$_4$ or H$_5$IO$_6$ |

R = H or lower alkyl
X = electron withdrawing group such as Br, Cl, and I.

Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R) or (S), or as (D) or (L) for amino acids. The present invention is meant to comprehend all such possible diastereomers as well as their racemic and optically pure forms. Optically active (R) and (S), or (D and L), isomers may be prepared using chiral synthons or chiral reagents, or resolved using conventional techniques. When the compounds described herein contain olefinic double bonds, and unless specified otherwise, it is intended to include both E and Z geometric isomers.

Salts

The pharmaceutical compositions of the present invention comprise a compound of Formula II as an active ingredient or a pharmaceutically acceptable salt thereof, and may also contain a pharmaceutically acceptable carrier and, optionally, other therapeutic ingredients. The term "pharmaceutically acceptable salts" refers to salts prepared from pharmaceutically acceptable non-toxic acids or bases including organic and inorganic acids or bases.

When a compound of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucosamine, morpholine, piperazine, piperidine, polyamine resins, procaine, purine, theobromine, triethylamine, trimethylamine, tripropylamine, etc.

When a compound of the present invention is basic, salts may be prepared from pharmaceutically acceptable non-toxic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Particularly preferred are citric, hydrobromic, maleic, phosphoric, sulfuric, and tartaric acids.

In the discussion of methods of treatment herein, reference to the compounds of Formula II is meant to also include the pharmaceutically acceptable salts thereof.

Utilities

The ability of the compounds of Formula II to inhibit serine proteases makes them useful for preventing or reversing the symptoms induced by these enzymes in a mammal. This enzyme inhibition indicates that the compounds are useful to treat, prevent, or ameliorate hyper-coagulation disease in mammals, especially in humans, and are useful in post-myocardial infarction treatment and in post-angioplasty treatment.

The ability of compounds to inhibit metallo proteases such as angiotensin converting enzyme makes them useful for preventing or reversing the symptoms induced by these enzymes in a mammal. This enzyme inhibition indicates that the compounds are useful to treat, prevent, or ameliorate hypertension in mammals, especially in humans.

The ability of the compounds of Formula II to inhibit carbonic anhydrase isozymes makes them useful for preventing or reversing the symptoms induced by these enzymes in a mammal. This enzyme inhibition indicates that the compounds are useful to treat, prevent, or ameliorate ocular diseases, particularly glaucoma in mammals, especially in humans.

Dose Ranges

The magnitude of the prophylactic or therapeutic dose of the compounds of Formula II will vary with the nature and severity of the condition to be treated and with the particular compound of Formula II and its route of administration. In general, the daily dose range for anti-enzymic use lies in the range of 20 to 0.001 mg/kg body weight of a mammal, preferably 10 to 0.01 mg/kg, and most preferably 1.0 to 0.1 mg/kg, in single or divided doses. In some cases, it may be necessary to use doses outside these ranges.

When a composition for intravenous administration is employed, a suitable daily dosage range is from about 10 to 0.0005 mg (preferably 5 to 0.01 mg) compound of Formula II per kg body weight.

When a composition for oral administration is employed, a suitable daily dosage range is from about 20 to 0.001 mg (preferably 10 to 0.01 mg) compound of Formula II per kg body weight.

When a composition for ophthalmic administration is employed, a suitable daily dosage range is from about 10–0.01% (preferably 5.0–0.5% compound of Formula II, typically prepared as a 2.0–0.1% by weight solution or suspension of a compound of Formula II in an acceptable ophthalmic formulation.

The compounds of Formula II may also be used in combination with other pharmaceutically active ingredients. For example, a typical ocular formulation may comprise the compound alone or in combination with a β-adrenergic blocking agent such as timolol maleate or a parasympathomimetic agent such as pilocarpine. When used in combination, the two active ingredients are present in approximately equal parts.

Pharmaceutical Compositions

Any suitable route of administration may be employed for providing a mammal, especially a human, with an effective dosage of a compound of Formula II. For example, oral, rectal, topical, parenteral, ocular, pulmonary, nasal, etc. routes may be employed. Dosage forms include tablets, troches, dispersions, suspensions, solutions, capsules, creams, ointments, aerosols, and the like.

The pharmaceutical compositions of the present invention comprise a compound of Formula II, or a pharmaceutically acceptable salt thereof, as an active ingredient, and may also contain a pharmaceutically acceptable carrier and, optionally, other therapeutically active ingredients.

The compositions include compositions suitable for oral, rectal, topical (including transdermal devices, aerosols, creams, ointments, lotions, and dusting powders), parenteral (including subcutaneous, intramuscular, and intravenous), ocular (ophthalmic), pulmonary (nasal or buccal inhalation), or nasal administration; although the most suitable route in any given case will depend largely on the nature and severity of the condition being treated and on the nature of the active ingredient. They may be conveniently presented in unit dosage form and prepared my any of the methods well known in the art of pharmacy.

A compound of Formula II may be combined as the active ingredient in intimate admixture with a pharmaceutical carrier according to conventional pharmaceutical compounding techniques. The carrier may take a wide variety of forms depending on the nature of the preparation desired for administration, i.e., oral, parenteral, etc. In preparing oral dosage forms, any of the usual pharmaceutical media may be used, such as water, glycols, oils, alcohols, flavoring agents, preservatives, coloring agents, and the like in the case of oral liquid preparations (e.g., suspensions, elixirs, and solutions); or carriers such as starches, sugars, microcrystalline cellulose, diluents, granulating agents, lubricants, binders, disintegrating agents, etc. in the case of oral solid preparations such as powders, capsules, and tablets. Solid oral preparations are preferred over liquid oral preparations. Because of their ease of administration, tablets and capsules are the preferred oral dosage unit form. If desired, capsules may be coated by standard aqueous or non-aqueous techniques.

In addition to the dosage forms described above, the compounds of Formula II may be administered by controlled release means and devices such as those described in U.S. Pat. Nos. 3,536,809; 3,598,123; 3,630,200; 3,845,770; 3,916,899; and 4,008,719, which are incorporated herein by reference.

Pharmaceutical compositions of the present invention suitable for oral administration may be prepared as discrete units such as capsules, cachets, or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general, the compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent, or surface active or dispersing agent. Molded tablets may be made by molding in a suitable machine, a mixture of the powdered compound moistened with an inert liquid diluent. Opthalmic inserts are made from compression molded films which are prepared on a Carver Press by subjecting the powdered mixture of active ingredient and HPC to a compression force of 12,000 lb.(gauge) at 149° C. for 1–4 min. The film is cooled under pressure by having cold water circulate in the platen. The inserts are then individually cut from the film with a rod-shaped punch. Each insert is placed in a vial, which is then placed in a humidity cabinet (88% relative humidity at 30° C.) for 2–4 days. After removal from the cabinet, the vials are capped and then autoclaved at 121° C. for 0.5 hr.

The following are representative pharmaceutical dosage forms of the compounds of Formula II:

| I.M. Injectable Suspension | mg/mL |
|---|---|
| Compound of Formula II | 10 |
| Methylcellulose | 5 |
| Tween 80 | 0.5 |
| Benzyl alcohol | 9 |
| Benzalkonium chloride | 1 |
| Water for injection to a total volume of 1 mL | |
| Tablet | mg/tablet |
| Compound of Formula II | 25 |
| Microcrystalline cellulose | 415 |
| Povidone | 14 |
| Pregelatinized starch | 43.5 |
| Magnesium stearate | 2.5 |
| | 500 |
| Capsule | mg/capsule |
| Compound of Formula II | 25 |
| Lactose powder | 573.5 |
| Magnesium stearate | 1.5 |
| | 600 |
| Aerosol | Per canister |
| Compound of Formula II | 24 mg |
| Lecithin, NF liquid concentrate | 1.2 mg |
| Trichlorofluoromethane, NF | 4.025 gm |
| Dichlorodifluoromethane, NF | 12.15 gm |
| Opthalmic Solution | mg/mL |
| Compound of Formula II | 1 |

-continued

| | |
|---|---|
| Monobasic sodium phosphate.2H$_2$O | 9.38 |
| Dibasic sodium phosphate.2H$_2$O | 28.48 |
| Benzalkonium chloride | 1 |
| Water for injection to a total volume of 1 mL | |
| Opthalmic Suspension | mg/g |
| | |
| Compound of Formula II | 1 |
| Petrolatum liquid to a total weight of 1 g | |
| Opthalmic Insert | mg/insert |
| | |
| Compound of Formula II | 1 |
| Hydroxypropylcellulose | 12 |

These compounds may also be used as libraries for discovering new lead structures by evaluation across an array of biological assays, including the discovery of selective inhibition patterns across isozymes. These libraries are thus tools for drug discovery; i.e., as a means to discover novel lead compounds by screening the libraries against a variety of biological targets and to develop structure-activity relationships in large families of related compounds. The libraries may be tested with the ligands attached to the solid supports as depicted in Formula I or the individual compounds II may be detached prior to evaluation. With the compounds of Formula I, screening assays such as FACS sorting and cell lawn assays may be used. When a compound is detached prior to evaluation, its relationship to its solid support is maintained, for example, by location within the grid of a standard 96-well plate or by location of activity on a lawn of cells. The solid support associated with bioactivity or the solid support related to the detached ligand may then be decoded to reveal the structural or synthetic history of the active compound (Ohlmeyer et al., *Proc. Natl. Acad. Sci. USA*, 90, 10922–10926, December 1993).

Assays for Determining Biological Activity

Xanthine Oxidase Inhibition—The following materials are used:

- 3.9 µM hypoxanthine
- 0.3 µM 4aminoantipyrene
- 2 mM 3,5-dichloro-2-hydroxybenzenesulfonate
- 50 mM sodium phosphate buffer, pH 7.5
- 5 U/mL horseradish peroxidase (Sigma P-6782, 5500 U/5 mg)
- 3 nM xanthine oxidase (buttermilk, Sigma X4500, 16 U/mL) inhibitor Reactions are carried out in 24 µL total volume in 96-well U-bottom polypropylene microtiter dishes (Costar) containing the test compounds. 8 µL of sodium phosphate buffer, pH 7.5, is added to each well. A substrate mixture is prepared on ice by mixing 0.53 mL sodium phosphate buffer, 0.4 mL 4-aminoantipyrene (0.61 mg/mL), 0.4 mL 3,5-dichloro-2-hydroxybenzene-sulfonate (5.3 mg/mL), 4 µL horseradish peroxidase (Sigma P-6782, 5500 U/5 mg), and 128 µL hypoxanthine 920 µ/mL. 8 µL of the substrate mixture is then pipetted into each well. 8 µL xanthine oxidase (buttermilk, 9.0 nM, Sigma X-4500, 16 U/mL) in sodium phosphate buffer, pH 7.5 (or buffer alone as a control) is added last, directly into the reaction mixture. The plates are pulse-spun briefly in a tabletop centrifuge before reading absorbance. Absorbance is read using a dual kinetics program (490 minus 650 nm) for 15 min. at r.t. without automix, in at microplate reader (Molecular Devices Thermomax). Initial rates are calculated (Vmax program) and compared to those of reactions without inhibitor.

Other assays for evaluating the compounds of the present invention are well known in the art. Representative examples of references teaching these assays follow:

ACE Inhibition—Holmquist et al, "A Continuous Spectrophotometric Assay for Angiotensin Converting Enzyme", *Anal. Biochem.*, 95, 540–548 (1979).

Thrombin Inhibition—Lottenberg et al., "Assay of Coagulation Proteases Using Peptide Chromogenic and Fluorogenic Substrates", *Meth. in Enzymol.*, 80, 341–361, (1981).

Carbonic Anhydrase Inhibition—Maren and Couto, "The Nature of Anion Inhibition of Human Red Cell Carbonic Anhydrases", *Archiv. of Biochem. and Biophy.*, 196, No. 2, September, 501–510 (1979).

Carbonic Anhydrase Inhibition—Ponticello et al, "Thienothiopyran-2-sulfonamides: A Novel Class of Water-Soluble Carbonic Anhydrase Inhibitors", *J. Med. Chem.*, 30, 591597 (11987).

Methods of Synthesis

The compounds of the present invention can be prepared according to the following methods. At each step in the synthesis each solid support upon which a compound is being synthesized is uniquely tagged to define the particular chemical event(s) occurring during that step. The tagging is accomplished using identifiers such as those of Formula IV, which record the sequential events to which the support is exposed during the synthesis, thus providing a reaction history for the compound produced on each support. The identifiers are used in combination with one another to form a binary or higher order encoding scheme permitting a relatively small number of identifiers to encode a relatively large number of reaction products. For example, when used in a binary code, N identifiers can encode up to $2^N$ different compounds and/or conditions. By associating each variable or combination of variables at each step of the synthesis with a combination of identifiers which uniquely define the chosen variables such as reactant, reagent, reaction conditions, or combinations of these, one can use the identifiers to define the reaction history of each solid support.

In carrying out the syntheses, one begins with at least $10^3$, desirably at least $10^4$, and generally not exceeding $10^{15}$ solid supports. Depending on the pre-determined number of $R^1$ choices for the first step, one divides the supports accordingly into as many containers. The appropriate reagents and reaction conditions are applied to each container and the combination of identifiers which encode for each $R^1$ choice is added and attached. Depending on the chemistries involved, the tagging may be done prior to, concomitantly with, or after the reactions which comprise each choice. As a control, sample supports may be picked at any stage and a portion of their tags detached and decoded to verify that the correct tags are bound to the sample supports. As needed, one may wash the beads free of any excess reagents or by-products before proceeding. At the end of each step, the supports are combined, mixed, and again divided, this time into as many containers as pre determined for the number of A choices for the second step in the synthesis. This procedure of dividing, reacting, tagging, and remixing is repeated until the combinatorial synthesis is completed.

Scheme 1

Functionalized supports such as amino-functionalized or hydroxy-terminating PEG grafted polystyrene beads are equally divided into a pre-determined number of reaction vessels and are reacted with either a) a cleavable linker/ligand element which has been pre-formed to generate 2 when the detached ligand element terminates in OH or b) a cleavable linker, followed by reaction with a ligand element to generate 3 in the case when the detached ligand element terminates in COOH. Compounds 2 and 3 are then treated with piperidine/DMF to de-protect the amino group of the ligand element $R^1$ to yield 4 (Scheme 1, step (c)). Unique tagging of the supports in each reaction vessel is achieved with combinations of identifiers encoded in a binary scheme, e.g., as depicted in Table 1-1 for seven choices of $R^1$. The identifiers are attached by adding a solution of the identifiers (in a 5% wt./wt. identifier:solid support ratio) to a batch of supports suspended in $CH_2Cl_2$ and shaking the mixture for 30 min. A dilute solution of rhodium trifluoroacetate dimer is added and the mixture is immediately shaken. The mixture is continued to be shaken overnight and the washed in $CH_2Cl_2$.

Scheme 2

The compounds 4 are pooled, mixed, and then divided into a pre-determined number of reaction vessels, each of which is treated with one reagent corresponding to ligand element A, in the presence of HOBt/DMF to produce 5. The reaction vessels are then treated with piperidine/DMF to de-protect the terminal amino group, yielding 6. Unique tagging of the supports in each reaction vessel is achieved with combinations of additional identifiers encoded in a binary scheme, e.g., as depicted in Table 1-2 for 31 choices of A.

Scheme 3

The compounds 6 are pooled, mixed, and then divided into a pre-determined number of reaction vessels each of which is treated with one reagent corresponding to ligand element Y in the presence of solvents such as $CH_2Cl_2$ and DMF, and, when required, condensation reagents such as DIC, acylation catalysts such as DMAP, and bases such as triethylamine to produce 7. Unique tagging of the supports in each reaction vessel is achieved with combinations of additional identifiers encoded in a binary scheme, e.g., as in Table 1-3 for 31 choices of Y. Compound 7 is then either exposed to UV light (~360 nm) in a lower alkanol such as MeOH to cleave the protected form of the compounds of Formula II from the support/linker complex or first treated with TFA/thioanisole/EDT to remove the protecting groups on the $R^2$ sidechains and then exposed to UV light in a lower alkanol such as MeOH to cleave compound II.

SCHEME 1
ADDITION OF $R^1$ a. Carbonate-linked Moieties

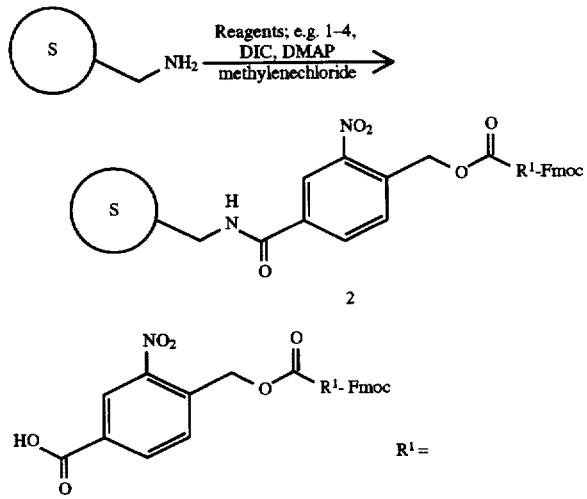

b. Ester-linked Moieties

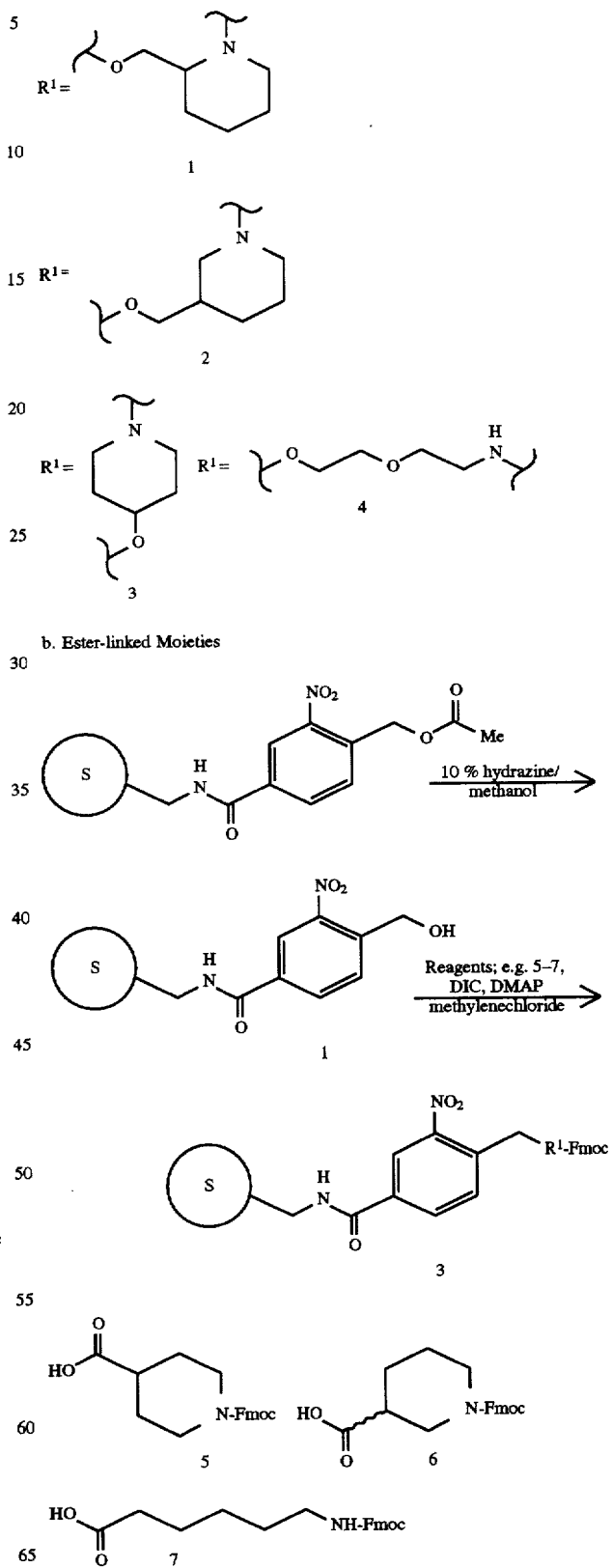

-continued
SCHEME 1
ADDITION OF R[1]

c. Fmoc Deprotection 2,3 →(50% piperidine/DMF)→

SCHEME 2
ADDITION OF A

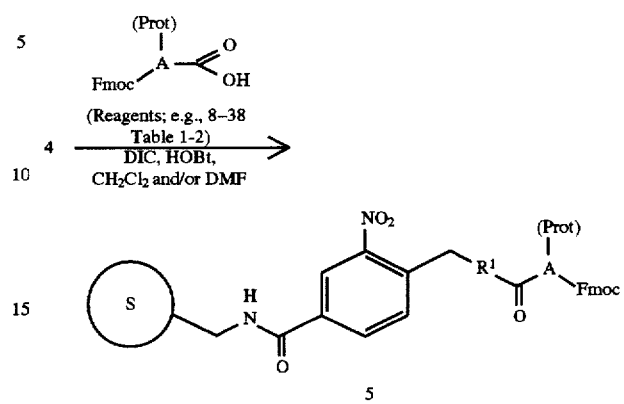

4 →(Reagents; e.g., 8–38 Table 1-2) DIC, HOBt, CH$_2$Cl$_2$ and/or DMF→ 5

5 →(50% piperidine/DMF)→

SCHEME 3
ADDITION OF Y

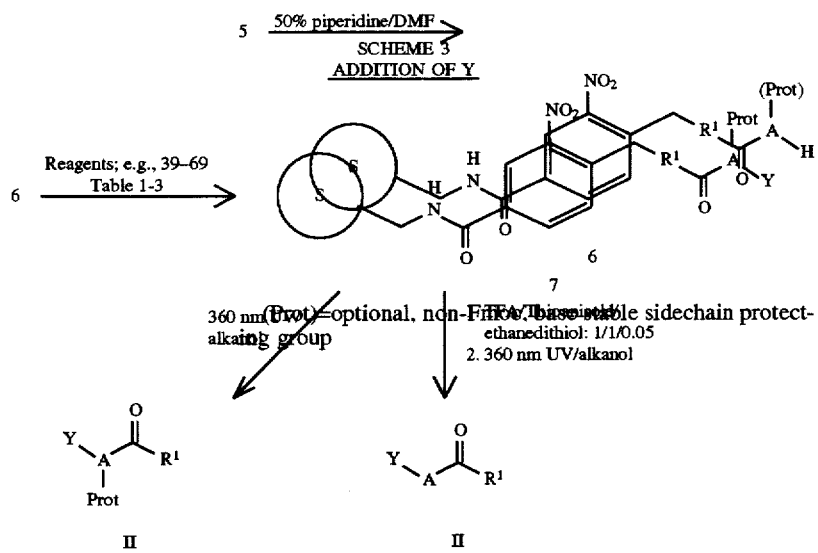

6 →(Reagents; e.g., 39–69 Table 1-3)→ 7

(Prot) = optional, non-Fmoc/base-stable sidechain protecting group 360 nm

1. TFA/thioanisole/ethanedithiol: 1/1/0.05
2. 360 nm UV/alkanol

II        II

-continued
SCHEME 1
ADDITION OF R[1]

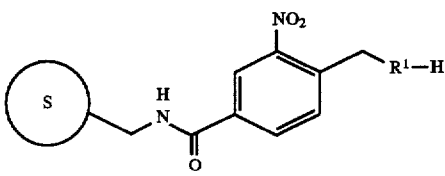

4*

* where R[1] includes the carbonate linkage in 2 and the ester linkage in 3

Representative Compounds

Table 2 illustrates compounds of Formula II which are representative of the present invention:

Y—A—CO—R[1]      II

TABLE 2
REPRESENTATIVE COMPOUNDS

| | Y | A | R¹ |
|---|---|---|---|
| 1. | 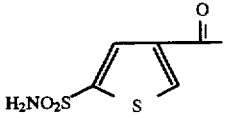 | —NH(CH₂)₂— | —NH(CH₂)₂O(CH₂)₄OH |
| 2. | 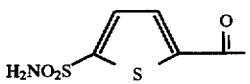 | —NH(CH₂)₃— | —NH(CH₂)₃COOH |
| 3. | 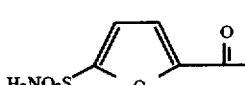 | —NH(CH₂)₅— | —NH(CH₂)₄OH |
| 4. | 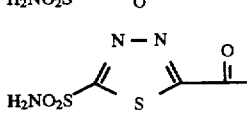 | —NH(CH₂)₁₀— | 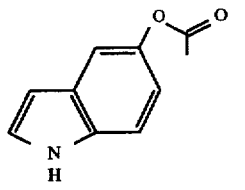 |
| 5. | 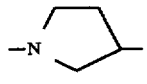 | 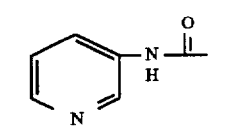 | 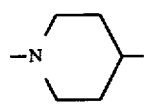 |
| 6. | 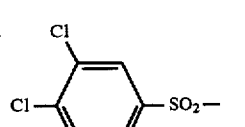 | 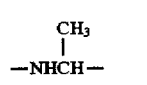 | 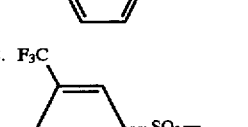 |
| 7. | 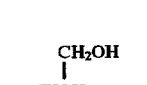 | CH₃<br>|<br>—NHCH— | 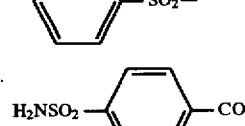(CH₂)₄—CO₂H |
| 8. | 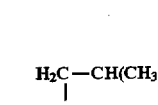 | CH₂OH<br>|<br>—NHCH— | CH₃<br>|<br>—N—(CH₂)₄—OH |
| 9. | 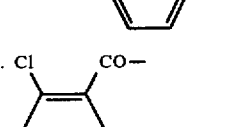 | H₂C—CH(CH₃)₂<br>|<br>—NHCH— | 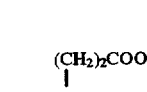CH₂OH |
| 10. |  | (CH₂)₂COOH<br>|<br>—NHCH—<br>(L) | —N⟨⟩CH₂OH |

Table 3 illustrates additional compounds of Formula II representative of the present invention which are inhibitors of carbonic anhydrase:

TABLE 3
REPRESENTATIVE COMPOUNDS

| | Y | A | R¹ |
|---|---|---|---|
| 1. | 4-(H₂NSO₂)-C₆H₄-CO- | -NHCH(CH₂CH(CH₃)₂)- (L) | 3-carboxypiperidin-1-yl |
| 2. | 4-(H₂NSO₂)-C₆H₄-CO- | -NH-CH(CH₂Ph)- (L) | 3-(hydroxymethyl)piperidin-1-yl |
| 3. | 2,5-dichloro-4-(SO₂NH₂)-C₆H₂-CO- | -NH-CH((CH₂)₂-COOH)- (L) | 3-(hydroxymethyl)piperidin-1-yl |
| 4. | 2,5-dichloro-4-(SO₂NH₂)-C₆H₂-CO- | -NH-(CH₂)₅- | 3-(hydroxymethyl)piperidin-1-yl |
| 5. | 4-(H₂NSO₂)-C₆H₄-CO- | -NH-CH(CH₂Ph)- | -NH-(CH₂)₅-COOH |
| 6. | 4-(H₂NSO₂)-C₆H₄-CO- | -NHCH(CH₂CH(CH₃)₂)- (L) | 3-carboxypiperidin-1-yl |
| 7. | 2,5-dichloro-4-(SO₂NH₂)-C₆H₂-CO- | -NH-CH(CH₂Ph)- (L) | 3-carboxypiperidin-1-yl |
| 8. | 2,5-dichloro-4-(SO₂NH₂)-C₆H₂-CO- | -NH-CH(CH₃)- (D) | -NH-(CH₂)₅-COOH |
| 9. | 4-(H₂NSO₂)-C₆H₄-CO- | -NH-CH(CH₂COOH)- (D) | 3-carboxypiperidin-1-yl |

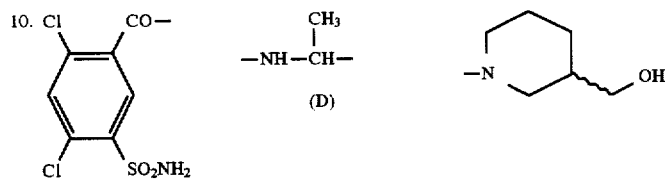
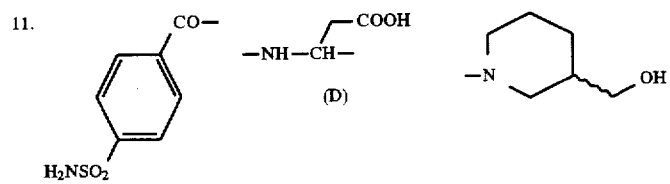
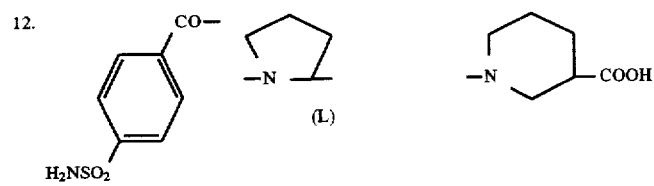
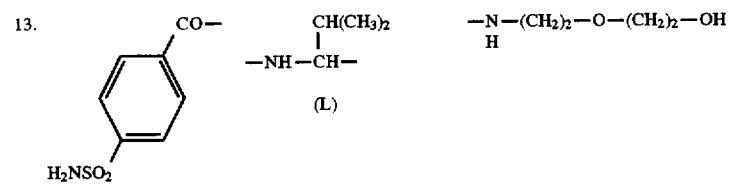
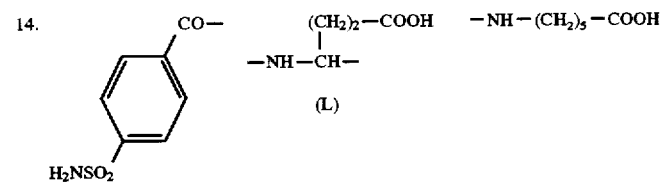
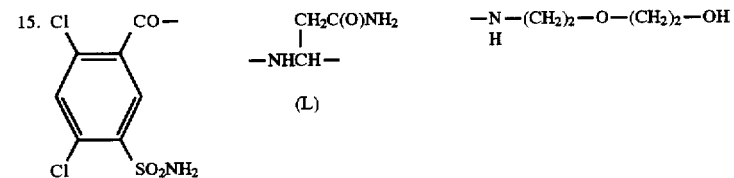
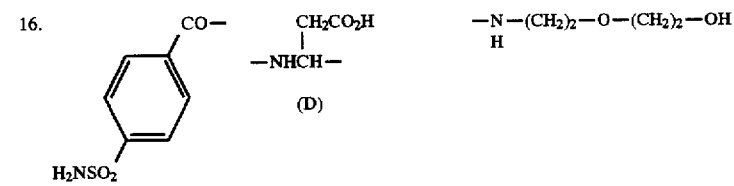
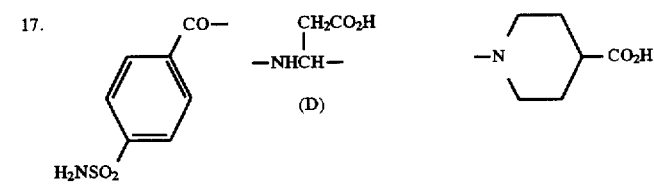
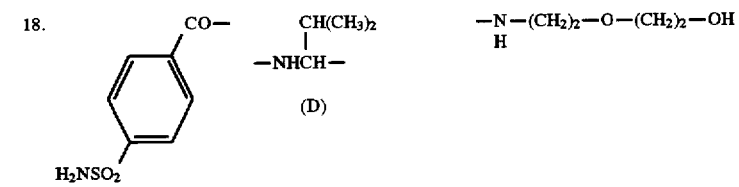

19. 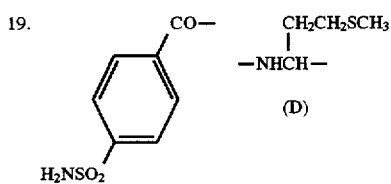 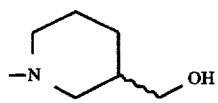
20. 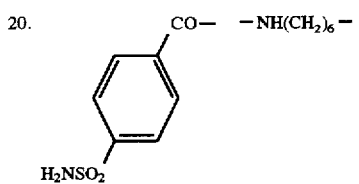 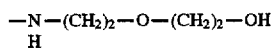
21. 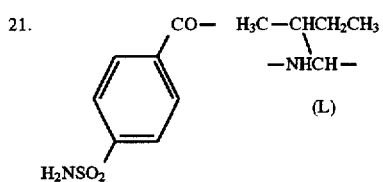 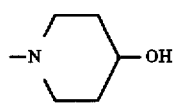
22. 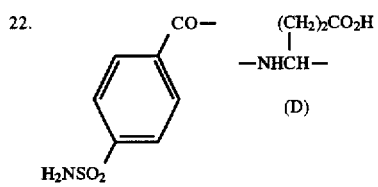 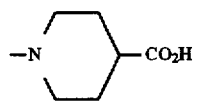
23. 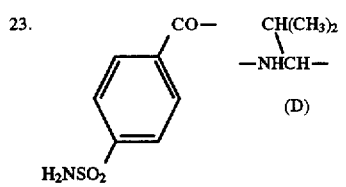 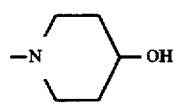
24. 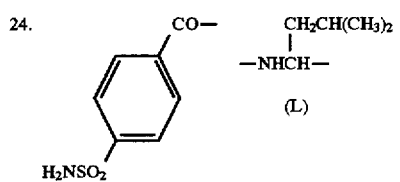 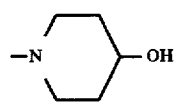
25. 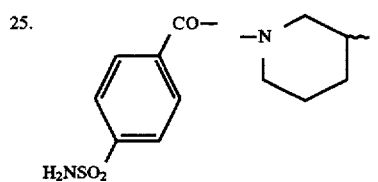 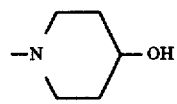
26. 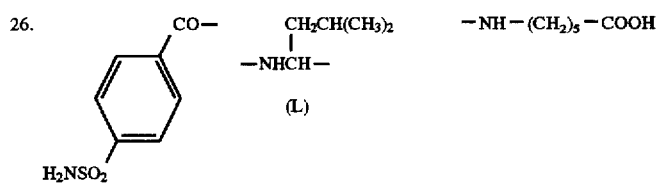
27. 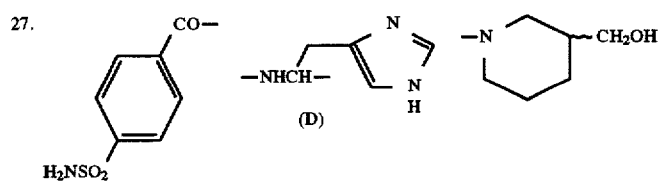

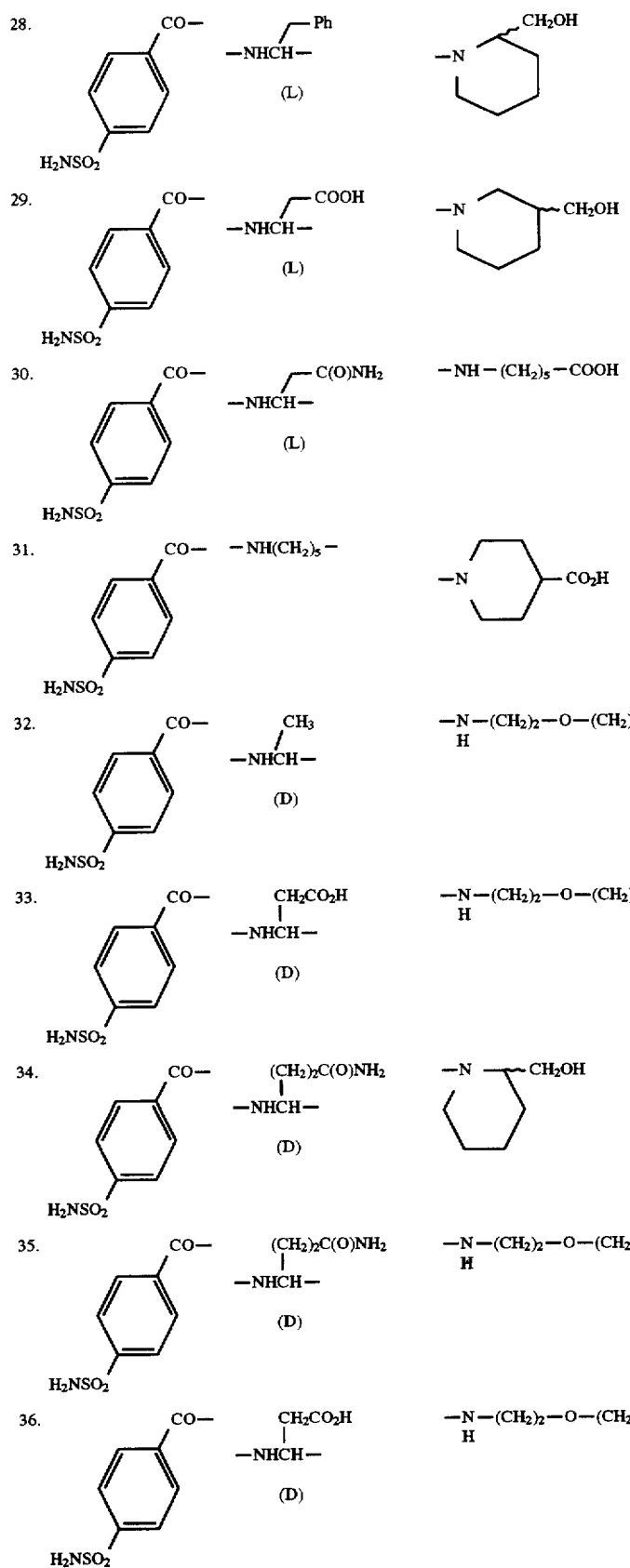

The invention is further defined by reference to the following examples, which are intended to be illustrative and not limiting.

PREPARATION 1

IDENTIFIERS

Thirteen compounds of the general formula:

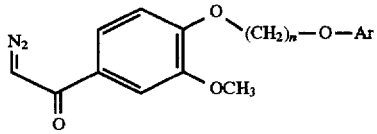

wherein:

n=3–12 and Ar is pentachlorophenyl or
n=4–6 and Ar is 2,4,6-trichlorophenyl were prepared according to Scheme 4 and the following, illustrative example.

a) Methyl vanillate (0.729 g, 4.0 mmole), 1-hydroxy-9-(2,3,4,5,6-pentachlorophenoxy)nonane (1.634 g, 4.0 mmole) and triphenylphosphine (1,258 g, 4.8 mmole) were dissolved in 20 mL dry toluene under argon. DEAD (0.76 mL, 0.836 g, 4.8 mmole) was added dropwise and the mixture was stirred at 25° C. for one hr. The solution was concentrated to half volume and purified by flash chromatography eluting with DMC to give 1.0 g (1.7 mmole, 43%) of the product as a white crystalline solid.

b) The methyl ester from Step (a) (1.0 g, 1.7 mmole) was dissolved in 50 mL THF, 2 mL water was added, followed by LiOH (1.2 g, 50 mmole). The mixture was stirred at 25° C. for one hr. then refluxed for 5 hr. After cooling to 25° C., the mixture was poured onto ethyl acetate (200 mL) and the solution was washed with 1M HCl (3×50 mL) then sat'd aq. NaCl (1×50 mL) and dried over sodium sulfate. The solvent was removed and the crude acid azeotroped once with toluene.

c) The crude material from Step (b) was dissolved in 100 mL toluene, 10 mL (1.63 g, 14 mmole) thionyl chloride was added, and the mixture was refluxed for 90 min. The volume of the solution was reduced to approx. 30 mL by distillation, then the remaining toluene was removed by evaporation. The crude acid chloride was dissolved in 20 mL dry DCM and cooled to −70° C. under argon and a solution of approx. 10 mmole diazomethane in 50 mL anhydrous ether was added. The mixture was warmed to r.t. and stirred for 90 min. Argon was bubbled through the solution for 10 min., then the solvents were removed by evaporation and the crude material was purified by flash chromatography, eluting with 10–20% ethyl acetate in hexane. The diazoketone (0.85 g, 1.4 mmole, 82% yield over three steps) was obtained as a pale yellow solid.

An improvement was made to the final diazomethylation step, whereby the acid chloride was reacted with (trimethylsilyl)diazomethane and triethylamine to give the identifier, which was then used without further purification. This was a significant improvement over the original reaction with diazomethane, as the identifier was now obtained in high yield with no chlorometylketone byproduct. Also, purification by flash chromatography was no longer necessary, which in some cases had resulted in significant acid-catalyzed decomposition of the identifier.

Alternate Step c) To a solution of the acyl chloride (3.8 mmol, 1.00 eq.) and 1.85 mL (13.3 mmol, 3.50 eq.) of triethylamine in anhydrous THF/acetonitrile (1:1) at 0° C. under argon was added 5.7 mL (11.4 mmol, 3.00 eq.) of a 2.0M solution of (trimethylsilyl)diazomethane in hexanes. The resulting orange solution was stirred at 0° C. for 2 hr, then at 25° C. for 17 hr. (If a precipitate formed immediately upon addition of (trimethylsilyl)diazomethane, $CH_2Cl_2$ was added until the precipitate redissolved). EtOAc was added (250 mL), and the organic layer washed with saturated aq. $NaHCO_3$ (100 mL) and $H_2O$ (100 mL), then dried (anhydrous $MgSO_4$). Removal of the volatiles in vacuo gave the product as yellow crystals in 60–100% yield.

The other 12 identifiers of Formula IV were prepared by analogous synthetic routes, steps (a), (b), and (c).

In the synthesis of Example 1, the 13 identifiers were used to encode the combinatorial library. In Step 1, pentachlorophenyl identifiers where n=10–12 (abbreviated $C_{10}Cl_5$, $C_{11}Cl_5$, and $C_{12}Cl_{15}$) were used in the following binary encoding scheme: 001=(n=12), 010=(n=11) and 100=(n=10). In Step 2, pentachlorophenyl identifiers where n=5–9 (abbreviated $C_5Cl_5$, $C_6Cl_5$, $C_7Cl_5$, $C_8Cl_5$, $C_9Cl_5$) were used and encoded as follows: 00001=(n=9), 00010=(n=8), 00100=(n=7), 01000=(n=6) and 10000=(n=5). In Step 3, pentachlorophenyl identifiers where n=3–4 (abbreviated $C_3Cl_5$ and $C_4Cl_5$) were used and encoded as follows: 00001=(n=4), 00010=(n=3). Also in Step 3, trichlorophenyl identifiers where n=4–6 (abbreviated $C_4Cl_3$, $C_5Cl_3$, and $C_6Cl_3$) were used and encoded as follows: 00100=(n=6), 01000=(n=5), and 10000=(n=4).

Thus, in Step 1 reagent 3 (Table 1-1) is encoded "011" which represents tagging this choice in the synthesis with the two pentachloro-phenyl identifiers where n=11 and 12. Likewise, in Step 3 reagent 52 (Table 1-3) is encoded "01110" which represents tagging this choice in the synthesis with the pentachlorophenyl identifier where n=3 and the two trichlorophenyl identifiers where n=5 and 6.

SCHEME 4
IDENTIFIERS

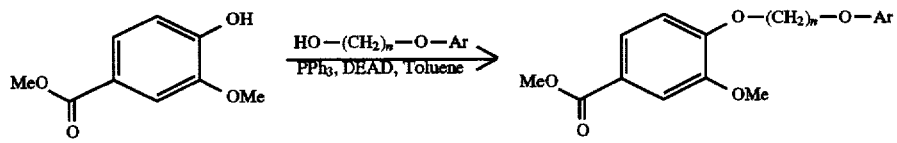

1. LiOH, THF/MeOH
2. $SOCl_2$, toluene reflux

-continued
SCHEME 4
IDENTIFIERS

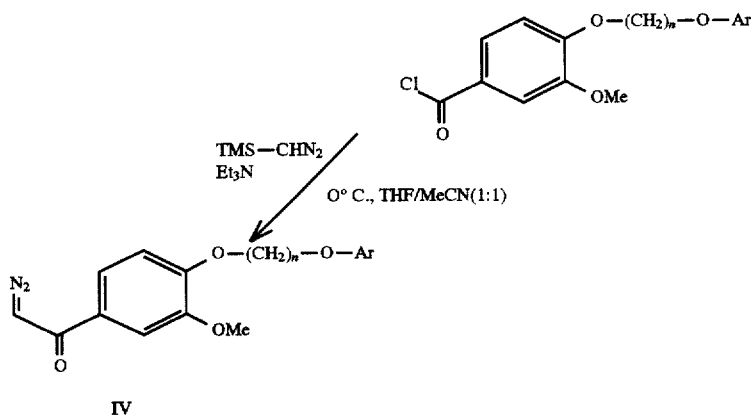

PREPARATION 2 t-BUTYL-4-(HYDROXYMETHYL)-3-NITROBENZOATE t-Butyl 4-(acetoxymethyl)-3-nitrobenzoate was prepared as described by Barany and Albericio, *J. Am. Chem. Soc.* 1.9 85, 107, 4936–4942. However, attempts to also follow the reference's final procedure for hydrazinolysis of the acetate using hydrazine hydrate in $CHCl_3$ at 25° C. produced only trace amounts of the desired hydroxymethyl final product, which is the t-butyl ester pre-cursor of the photocleavable linker used herein. It has now been found that hydrazinolysis using hydrazine hydrate in MeOH or DMF at 25° C. produces t-butyl 4-(hydroxymethyl)-3-nitrobenzoate in high yield but that a byproduct produced in DMF by additional diimide reduction of the nitro functionality to an amino group makes this solvent undesirable. Using MeOH as solvent, only the desired final product was obtained in near quantitative yield.

This new hydrazinolysis procedure was also used to produce the photocleavable linker when attached to Tenta-Gel S $NH_2$ resin.

t-Butyl 4-(hydroxymethyl)-3-nitrobenzoate: To a solution of 14.1 g (47.7 mmol, 1.00 eq.) of t-butyl 4-(acetoxymethyl)-3-nitrobenzoate in MeOH (200 mL) was added 27.0 mL (477 mmol, 10.0 eq.) of hydrazine hydrate (55% hydrazine). The resulting yellow solution was stirred at 25° C. for 4 hr. EtOAc (250 mL) and saturated aq. NaCl (85 mL) were added, and the organic layer collected after shaking. The organic layer was washed further with saturated aq. NaCl (2×85 mL, and then dried ($MgSO_4$). Removal of volatiles in vacuo gave the product in 93% yield as yellow crystals. The reaction is represented in Scheme 5.

TentaGel S $NR_2$— attached 4-(hydroxymethyl)-3-nitrobenzamide: See Example 1, Step 1a.

SCHEME 5
HYDRAZINOLYSIS

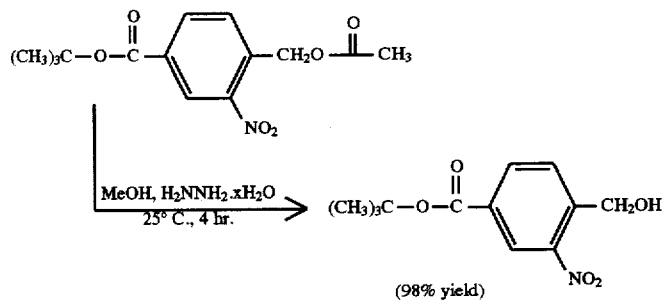

EXAMPLE 1

6727 COMPOUND LIBRARY

Step 1 a) Preparation of ester-linked resin batches

TentaGel S $NH_2$, (10 g, 2.9 mmole, 0.29 mmole/g) was suspended in 60 mL methylenechloride. 4-acetoxymethyl-3-nitrobenzoic acid (2.77 g, 11.6 mmole, 4 eq), DMAP (1.42 g, 11.6 mmole, 4 eq) and DIC (1.81 mL, 1.46 g, 11.6 mmole, 4 eq) was added in that order. The mixture was agitated at 25° C. with a wrist action shaker for 5 hours, at which time the resin gave a negative Kaiser test. The derivatized resin was washed (methylenechloride 5×50 mL, isopropanol 5×50 mL, then methylenechloride 5×50 mL), dried in vacuo and, stored in the dark.

The acetoxymethyl resin above was washed with methanol (1×150 mL), then suspended in 150 mL 10% hydrazine/methanol. The resin was agitated at 25° C. for 44 hours, filtered, then washed (methanol, 5×100 mL, then methylene chloride, 5×100 mL) and dried in vacuo.

Three batches of the above hydroxymethyl resin (3 g each, 0.84 mmole, 0.28 mmole/g) were placed in 100 mL synthesis vessels and each was suspended in 60 mL dichloromethane. One of N-Fmoc isonipecotic acid (0.885 g, 2.52 mmole, 3 eq), N-Fmoc nipecotic acid (0.885 g, 2.52 mmole, 3 eq), and N-Fmoc-ε-amino caproic acid (0.890 g, 2.52 mmole, 3 eq) was added to each of the three batches. DMAP (0.031 g, 0.252 mmole, 0.3 eq) and then DIC (0.4 mL, 0.318 g, 2.52 mmole, 3 eq) was added to each and the resin batches were agitated at 25° C. for 22 hours. The resin batches were filtered, washed (methylenechloride (5×50 mL) and isopropanol (2×50 mL), then methylenechloride (5×50 mL)), and dried in vacuo.

b) Preparation of carbonate-linked resin batches

N-Fmoc-2-hydroxymethylpiperidine (1.35 g, 4 mmole, 1 eq) was dissolved in 20 mL methylenechloride and cooled to 0° C. Phosgene (8 mL, 2M solution in toluene, 16 mmole, 4 eq) was added followed by 2,6-lutidine (1.86 mL, 1.71 g, 4 eq), then the mixture was stirred for 30 min. The mixture was concentrated on a rotary evaporator to give a viscous slurry and this residue was redissolved in 30 mL methylenechloride (the solution contained some undissolved solid). 'Butyl 4-hydroxymethyl-3-nitrobenzoate (0.51 g, 2 mmole, 0.5 eq) was added and the mixture was stirred at 25° C. for 2 hours. The crude reaction mixture was poured onto 200 mL ethyl acetate and this solution was washed with 1M HCl (2×100 mL), sat'd aq. $NaHCO_3$ (2×100 mL) and sat'd aq. NaCl (1×100 mL). The solution was dried over magnesium sulfate, filtered, and evaporated to give the crude product. This was purified by flash chromatography eluting with 10–30% ethylacetate/hexane to give the product (1.22 g, 1.97 mmole, 99%) as a pale yellow solid.

The carbonate above was dissolved in 20 mL methylene chloride, 10 mL TFA was added and the mixture was stirred at 25° C. for 16 hours. The solution was diluted with 50 mL toluene and evaporated to give the carboxylic acid as a viscous yellow oil which was azeotroped with toluene once, then dried in vacuo.

The acid prepared above (~2 mmole, 2 eq) was dissolved in 30 mL methylenechloride and this solution was added to TentaGel S $NH_2$ (3 g, 0.32 mmole/g, ~1 mmole, 1 eq). The resin was suspended by agitation then DMAP (40 mg, 0.3 mmole, 0.3 eq) and DIC (0.47 mL, 0.4 g, 3 eq) were added in that order. The resin was agitated at 25° C. for 19 hours, at which time it gave a negative Kaiser test. The resin was filtered and washed (methylenechloride 10×50 mL), then dried in vacuo.

The three other carbonate linked resin batches were prepared in an analogous manner using the reagents of Table 1-1.

c) Encoding of Step 1

One gram batches of the seven resin batches from Steps 1(a) and 1(b) with the appropriately linked N-Fmoc protected amino acid or amino alcohol were placed in seven separate synthesis vessels and each was suspended in 20 mL methylene chloride.

Stock solutions of 200 mg of $C_{12}C_5$, $C_{11}Cl_5$, and $C_{10}Cl_5$ -linker-diazoketone (Preparation 1) were prepared in 4 mL methylenechloride. Aliquots (1 mL) of the stock solutions were used to prepare the appropriate binary coding mixtures for each of the seven resin batches. The appropriate coding mixture was added to each resin batch and the resin was agitated for 1 hour. Rhodium trifluoroacetate dimer (1 mL of a 1 mg/mL solution in methylenechloride) was added to each of the vessels and the resin was agitated at 25° C. overnight. Each resin batch was washed with methylenechloride (1×50 mL), then the batches were combined and the entire library (seven compounds) was washed with methylenechloride (10×50 mL).

d) Deprotection

N-Fmoc protecting groups were removed by washing the resin once with DMF, filtering, then suspending the resin in 60 mL 50% piperidine/DMF and agitating at room temperature for 30 min. The resin was filtered, washed (DMF (5×50 mL) and methylenechloride (10×50 mL)) and dried in vacuo.

Step 2 a) Addition of A

The dried resin from Step 1(d) was divided into 31 batches of 210 mg (~0.07 mmole), each of which was placed in a 20 mL synthesis vessel. Each of the reagents (0.25 g,>0.4 mmole,>6 eq) (Table 1-2) used in the second step of the synthesis (N-Fmoc amino acid with acid labile side chain protection where appropriate) was dissolved in 10 mL methylenechloride. HOBt (1 mL of 1 mg/mL in DMF) was added and the solutions were shaken briefly. Further DMF was added to those amino acids that had not completely dissolved. Each reagent solution was added to one of the 31 resin batches. DIC (0.2 mL, ~1 mmole) was added to each vessel and the resin was agitated at 25° C. overnight. Each of the resin batches was filtered and washed separately (DMF (1×15 mL) and methylenechloride (10×15 mL)). The resin was suspended in 10 mL methylenechloride.

b) Encoding of Step 2

Stock solutions of 160 mg of $C_9Cl_5$, $C_8Cl_5$, $C_7Cl_5$, $C_6Cl_5$, and $C_5Cl_5$ -linker-diazoketone (Preparation 1) were prepared in 16 mL methylenechloride. Aliquots (1 mL) of the stock solutions were used to prepare the appropriate binary coding mixtures for each of the 31 resin batches (Table 1-2). The appropriate coding mixture was added to each of the resin batches and the resin was agitated for 30 min. Rhodium trifluoroacetate dimer (1 mL of a 1 mg/mL solution in methylenechloride) was added to each of the vessels and the resin was agitated at 25° C. overnight. Each resin batch was filtered then washed separately with methylenechloride (1×15 mL). The batches were combined and the entire library (217 compounds) was washed with methylenechloride (5×50 mL).

c) Deprotection

N-Fmoc protecting groups were removed by washing the resin once with DMF, filtering, then suspending the resin in 60 mL 50% piperidine/DMF and agitating at room temperature for 30 min. The resin was filtered, washed (DMF (5×50 mL) and methylenechloride (10×50 mL)) and dried in vacuo.

Step 3 a) Addition of Y

The dried resin from Step 2 (c) was divided into 31 batches of 150 mg (~0.05 mmole), each of which was placed in a 20 mL synthesis vessel. Each of the reagents (0.25 g,>0.4 mmole,>8 eq) used in the third step of the synthesis was dissolved in methylenechloride or DMF or a mixture of the two as appropriate (Table 1-3). Each reagent solution was added to one of the 31 resin batches, then any coreagents were added as required (see table). The resin batches were agitated at 25° C. overnight, then each was washed (DMF (1×10 mL) and methylenechloride (10×10 mL)).

b) Encoding of Step 3

Stock solutions of 200 mg of $C_4Cl_5$ and $C_3Cl_5$ -linker-diazoketone (Preparation 1) were prepared in 16 mL methylenechloride. Stock solutions of 600 mg of $C_6Cl_3$, $C_5Cl_3$, and $C_4Cl_3$ -linker-diazoketone (Preparation 1) were prepared in 16 mL methylenechloride. Aliquots (1 mL) of the stock solutions were used to prepare the appropriate binary coding mixtures for each of the 31 resin batches (Table 1-3).

The appropriate coding mixture was added to each of the resin batches and the resin was agitated for 30 min. Rhodium trifluoroacetate dimer (1 mL of a 1 mg/mL solution in methylenechloride) was added to each of the vessels and the resin was agitated at 25° C. overnight. Each resin batch was filtered then washed separately with methylenechloride (1×15 mL). The batches were combined and the entire library (6727 compounds) was washed with methylenechloride (5×50 mL), then dried in vacuo.

c) Deprotection

The combined resins from Step 3(b) (+2 g) were suspended in 60 mL TFA/thioanisole/EDT (50/50/5) and shaken at room temperature overnight. The resins were filtered, washed (methylenechloride 10×50 mL), and dried in vacuo.

d) Decoding Procedure

A bead is placed in a 1.3 mm diameter pyrex capillary with 2 µL of acetonitrile. Ceric ammonium nitrate solution (2 µL of a 0.1M aq. solution) and hexane (3 µL) are added and the two-phase mixture centrifuged briefly. The tube is sealed and left at 35° C. for 16 hrs, then opened. The organic layer is removed by syringe and mixed with 1 µL of N,O-bis(trimethylsilyl)acetamide. The silated tag solution (1 µL) is analyzed by GC with electron capture (EC) detection.

The GC analysis is performed with a Hewlett Packard 5890 plus gas chromatograph. On column injection into a 5 m, 0.32 mm retention gap connected to a 25 m, 0.2 mm crosslinked 5% phenylmethyl silicone column is used. The temperature and pressure programs for the analysis are 200°–320° C., 15° C./min, then 320° C. for 10 min and 20–40 psi at 2 psi/min, then 40 psi for 10 min. The EC detector is maintained at 400° C. and the auxiliary gas is set at 35 psi.

TABLE 1-1

R¹ Residues and Encoding Scheme

| R¹ Residue | Binary Code |
|---|---|
| 1. | 001 |
| 2. | 010 |
| 3. | 011 |
| 4. | 100 |
| 5. | 101 |

TABLE 1-1-continued

R¹ Residues and Encoding Scheme

| R¹ Residue | Binary Code |
|---|---|
| 6. | 110 |
| 7. | 111 |

TABLE 1-2

R² Reagents and Encoding Scheme

| Reagent | Binary Code |
|---|---|
| 8. (L) | 00001 |
| 9. (D) | 00010 |
| 10. SMe (D) | 00011 |
| 11. O$^t$Bu (L) | 00100 |
| 12. STrityl (L) | 00101 |
| 13. STrityl (L) | 00110 |
| 14. CO$_2$$^t$Bu (D) | 00111 |
| 15. CO$_2$$^t$Bu (D) | 01000 |

TABLE 1-2-continued

R² Reagents and Encoding Scheme

| Reagent | Binary Code |
|---|---|
| 16. (L) —NH—CH(CO₂ᵗBu side chain) | 01001 |
| 17. piperidinyl | 01010 |
| 18. (D) —NH—CH₂CH₂—C(=N-Trityl)=N— | 01011 |
| 19. (L) —NH—CH—CH₂—C(=N-Trityl)=N— | 01100 |
| 20. (L) —NH—CH—(CH₂)₄—NH-Boc | 01101 |
| 21. (D) —NH—CH—(CH₂)₄—NH-Boc | 01110 |
| 22. (L) —NH—CH—(CH₂)₃—NH—C(=NH)—NH-Mtr | 01111 |
| 23. (D) —NH—CH—(CH₂)₃—NH—C(=NH)—NH-Mtr | 10000 |
| 24. (D) —NH—CH—CH₂—C(=O)—NH-Trityl | 10001 |
| 25. (L) —NH—CH—CH₂—C(=O)—NH-Trityl | 10010 |
| 26. (L) —NH—CH—CH₂CH₂—C(=O)—NH-Trityl | 10011 |
| 27. (D) —NH—CH—CH₂CH₂—C(=O)—NH-Trityl | 10100 |
| 28. (L) —NH—CH—CH₂-(N-Boc-indol-3-yl) | 10101 |
| 29. (L) —NH—CH—CH(CH₃)—CH₂CH₃ | 10110 |
| 30. (L) —NH—CH—CH₂—Ph | 10111 |
| 31. —NH—CH₂— | 11000 |
| 32. (D) —NH—CH(CH₃)— | 11001 |
| 33. (D) —NH—CH(CH₃)₂ side | 11010 |
| 34. (L) —NH—CH(CH₃)₂ | 11011 |
| 35. (L) —NH—CH—CH₂—CH(CH₃)₂ | 11100 |
| 36. (D) —NH—CH—CH₂—CH(CH₃)₂ | 11101 |
| 37. —NH—(CH₂)₅CH₃ | 11110 |

TABLE 1-2-continued
R² Reagents and Encoding Scheme
| Reagent | Binary Code |
|---|---|
| 38. 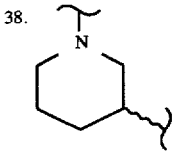 | 11111 |
TABLE 1-3
Y Reagents and Encoding Scheme
| Y Reagent | Solvent | Co-reagent(s) | Binary Code |
|---|---|---|---|
| 39. 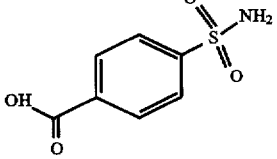 | DMF | 0.3 mL DIC, 100 mg DMAP | 00001 |
| 40. 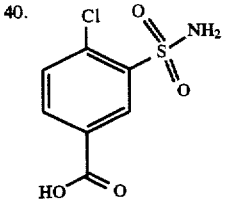 | DMF | 0.3 mL DIC, 100 mg DMAP | 00010 |
| 41. 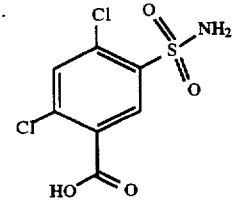 | DMF | 0.3 mL DIC, 100 mg DMAP | 00011 |
| 42. 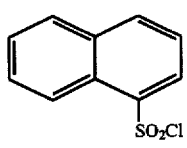 | $CH_2Cl_2$ | 0.5 mL $NEt_3$, 100 mg DMAP | 00100 |
| 43. 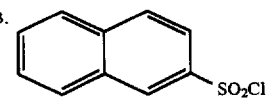 | $CH_2Cl_2$ | 0.5 mL $NEt_3$, 100 mg DMAP | 00101 |
| 44. 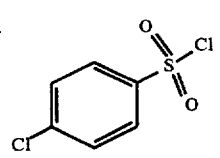 | $CH_2Cl_2$ | 0.5 mL $NEt_3$, 100 mg DMAP | 00110 |

TABLE 1-3-continued

Y Reagents and Encoding Scheme

| Y Reagent | Solvent | Co-reagent(s) | Binary Code |
|---|---|---|---|
| 45. 4-methylbenzenesulfonyl chloride | $CH_2Cl_2$ | 0.5 mL $NEt_3$, 100 mg DMAP | 00111 |
| 46. benzenesulfonyl chloride | $CH_2Cl_2$ | 0.5 mL $NEt_3$, 100 mg DMAP | 01000 |
| 47. 5-(dimethylamino)naphthalene-1-sulfonyl chloride | $CH_2Cl_2$/DMF (1:1) | 0.5 mL $NEt_3$, 100 mg DMAP | 01001 |
| 48. n-BuSO$_2$Cl | $CH_2Cl_2$ | 0.5 mL $NEt_3$, 100 mg DMAP | 01010 |
| 49. 4-tert-butylbenzenesulfonyl chloride | $CH_2Cl_2$ | 0.5 mL $NEt_3$, 100 mg DMAP | 01011 |
| 50. isopropylsulfonyl chloride | $CH_2Cl_2$ | 0.5 mL $NEt_3$, 100 mg DMAP | 01100 |
| 51. benzylsulfonyl chloride | $CH_2Cl_2$ | 0.5 mL $NEt_3$, 100 mg DMAP | 01101 |
| 52. biphenyl-4-carboxylic acid | $CH_2Cl_2$ | 0.3 mL DIC, 100 mg DMAP | 01110 |
| 53. biphenyl-2-carboxylic acid | $CH_2Cl_2$/DMF (1:1) | 0.3 mL DIC, 100 mg DMAP | 01111 |
| 54. 3-cyanobenzoic acid | $CH_2Cl_2$/DMF (1:1) | 0.3 mL DIC, 100 mg DMAP | 10000 |
| 55. glutaric anhydride | $CH_2Cl_2$ | 100 mg DMAP | 10001 |

TABLE 1-3-continued

Y Reagents and Encoding Scheme

| Y Reagent | Solvent | Co-reagent(s) | Binary Code |
|---|---|---|---|
| 56. nicotinic acid (pyridine-3-carboxylic acid) | $CH_2Cl_2$/DMF (1:1) | 0.3 mL DIC, 100 mg DMAP | 10010 |
| 57. $MeO-(CH_2)_5-CO_2H$ | $CH_2Cl_2$ | 0.3 mL DIC, 100 mg DMAP | 10011 |
| 58. benzoic acid | $CH_2Cl_2$ | 0.3 mL DIC, 100 mg DMAP | 10100 |
| 59. $H_3C\frown CO_2H$ | $CH_2Cl_2$ | 0.3 mL DIC, 100 mg DMAP | 10101 |
| 60. indole-3-acetic acid | $CH_2Cl_2$/DMF (1:1) | 0.3 mL DIC, 100 mg DMAP | 10110 |
| 61. N-acetyl-asparagine | $CH_2Cl_2$/DMF (1:1) | 0.3 mL DIC, 100 mg DMAP | 10111 |
| 62. imidazole-4-acetic acid | $CH_2Cl_2$/DMF (1:1) | 0.3 mL DIC, 100 mg DMAP | 11000 |
| 63. 4-(trifluoromethyl)phenyl isocyanate | $CH_2Cl_2$ |  | 11001 |
| 64. phenyl isocyanate | $CH_2Cl_2$ |  | 11010 |
| 65. isopropyl chloroformate | $CH_2Cl_2$ | 0.5 mL $NEt_3$ | 11011 |
| 66. 4-chlorophenyl isocyanate | $CH_2Cl_2$ |  | 11100 |
| 67. 2-naphthalenesulfonyl-glycine | Fmoc-G-OH, DIC, DMAP DMF, then piperidine/DMF | 2-Napthalene-sulfonyl chloride, $NEt_3$, DMAP, $CH_2Cl_2$ | 11101 |
| 68. 4-biphenylcarbonyl-glycine | Fmoc-G-OH, DIC, DMAP DMF, then piperidine/DMF | 4-Biphenyl-carboxylic acid, DIC, DMAP, $CH_2Cl_2$/DMF | 11110 |

TABLE 1-3-continued

Y Reagents and Encoding Scheme

| Y Reagent | Solvent | Co-reagent(s) | Binary Code |
|---|---|---|---|
| 69. (imidazole-CH₂-C(O)-NH-CH₂-CO₂H structure) | Fmoc-G-OH, DIC, DMAP DMF, then piperidine/ DMF | Imidazole-acetic acid, DIC, DMAP, CH₂Cl₂/DMF | 11111 |

EXAMPLE 2

DVB-CROSSLINKED VS. PEG-GRAFTED POLYSTYRENE SOLID SUPPORTS

A compound of Formula II of the structure V:

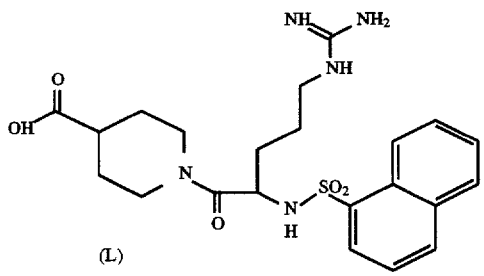

(L)

was synthesized essentially as described in Example 1, but without the addition of identifiers. The synthesis was carried out using both 100 μm 1% DVB-crosslinked polystyrene beads and 130 μm DVB-crosslinked, PEG-grafted polystyrene beads. At the end of each step, the ligand, or intermediate ligand, was cleaved from a portion of the beads. At the end of Step 3, a portion of the ligand on the PEG-grafted support was cleaved while still protected and another portion was de-protected prior to cleavage. The ligand on the DVB-crosslinked support was de-protected prior to cleavage. Table 2-1 presents the yield data for both syntheses. The yields were calculated based on the available functionalities (~300 pmole) on each bead.

TABLE 2-1

| | Comparative Yields | |
|---|---|---|
| | DVB Polystyrene (%) | PEG Polystyrene (%) |
| Step 1 | 49 | 85 |
| Step 2 | 31 | 45 |
| Step 3 | | |
| Protected | | 58 |
| De-protected | 8 | 61 |

What is claimed is:

1. A process for preparing t-butyl 4-(hydroxymethyl)-3-nitrobenzoate from t-butyl 4-(acetoxymethyl)-3-nitrobenzoate which comprises reacting t-butyl 4-(acetoxymethyl)-3-nitrobenzoate with hydrazine or hydrazine hydrate in a lower alkanol at 0°–50° C.

2. A process according to claim 1 wherein said lower alkanol is methanol.

3. A process according to claim 1 wherein said lower alkanol is isopropanol.

4. A process for preparing t-butyl 4-(hydroxymethyl)-3-nitrobenzoate from t-butyl 4-(acetoxymethyl)-3-nitrobenzoate which comprises reacting t-butyl 4-(acetoxymethyl)-3-nitrobenzoate with hydrazine or hydrazine hydrate in acetonitrile at 0°–50° C.

* * * * *